United States Patent
Beebe et al.

(10) Patent No.: US 7,112,444 B2
(45) Date of Patent: Sep. 26, 2006

(54) METHOD OF PERFORMING GRADIENT-BASED ASSAYS IN A MICROFLUIDIC DEVICE

(75) Inventors: David J. Beebe, Madison, WI (US); Glenn M. Walker, Brentwood, TN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/422,236

(22) Filed: Apr. 24, 2003

(65) Prior Publication Data

US 2004/0063151 A1    Apr. 1, 2004

Related U.S. Application Data

(60) Provisional application No. 60/375,156, filed on Apr. 24, 2002.

(51) Int. Cl.
*G01N 35/08* (2006.01)

(52) U.S. Cl. .......................... 436/52; 436/53; 436/172; 436/177; 436/180; 422/81; 422/82; 422/82.08; 422/100

(58) Field of Classification Search ............... 137/3, 137/93; 156/292, 273.5; 422/50, 58, 100, 422/81–82.08, 103; 435/6–7.2; 436/518, 436/514, 52, 53, 172, 177, 180
See application file for complete search history.

(56) References Cited

U.S. PATENT DOCUMENTS

| | | | |
|---|---|---|---|
| 3,692,486 A | 9/1972 | Glenn | 23/230 |
| 4,012,198 A | 3/1977 | Finter et al. | 23/253 |
| 5,716,852 A | 2/1998 | Yager et al. | 436/172 |
| 5,770,388 A | 6/1998 | Vorpahl | 435/7.25 |
| 5,869,004 A * | 2/1999 | Parce et al. | 422/100 |
| 5,932,100 A * | 8/1999 | Yager et al. | 210/634 |
| 5,942,443 A | 8/1999 | Parce et al. | 436/514 |
| 5,948,684 A | 9/1999 | Weigl et al. | 436/52 |
| 5,972,710 A * | 10/1999 | Weigl et al. | 436/34 |
| 6,004,515 A * | 12/1999 | Parce et al. | 422/100 |
| 6,046,056 A | 4/2000 | Parce et al. | 436/514 |
| 6,090,545 A * | 7/2000 | Wohlstadter et al. | 435/6 |
| 6,103,479 A * | 8/2000 | Taylor | 435/7.2 |
| 6,103,536 A | 8/2000 | Geisberg | 436/518 |
| 6,134,950 A * | 10/2000 | Forster et al. | 73/54.01 |
| 6,140,134 A | 10/2000 | Rittenburg | 436/514 |
| 6,150,180 A | 11/2000 | Parce et al. | 436/514 |
| 6,159,686 A | 12/2000 | Kardos et al. | 436/6 |

(Continued)

OTHER PUBLICATIONS

Dertinger et al., "Generation of Gradients Having Complex Shapes Using Microfluidic Networks," *Analytical Chemistry*, vol. 73, No. 6, Mar. 15, 2001, pp. 1240-1246.

(Continued)

*Primary Examiner*—Ong V. Le
*Assistant Examiner*—Nelson Yang
(74) *Attorney, Agent, or Firm*—Boyle Fredrickson Newholm Stein & Gratz S.C.

(57) ABSTRACT

A method is provided for performing a gradient-based assay in a microfluidic device. The method includes the steps of passing first and second fluids through a channel in the microfluidic device. The first fluid has a predetermined concentration of particles therein such that the particles in the first fluid diffuse into the second fluid so as to cause a gradient of concentration of particles in the second fluid as the second fluid flows through the channel. The second fluid sequentially intersects a series of targets along the channel wall as the second fluid flows through the channel.

8 Claims, 5 Drawing Sheets

U.S. PATENT DOCUMENTS

| | | | |
|---|---|---|---|
| 6,171,865 B1 * | 1/2001 | Weigl et al. | 436/52 |
| 6,176,962 B1 * | 1/2001 | Soane et al. | 156/292 |
| 6,200,814 B1 * | 3/2001 | Malmqvist et al. | 436/52 |
| 6,221,677 B1 * | 4/2001 | Wu et al. | 436/518 |
| 6,277,641 B1 | 8/2001 | Yager | 436/52 |
| 6,297,061 B1 | 10/2001 | Wu et al. | 436/518 |
| 6,306,590 B1 | 10/2001 | Mehta et al. | 436/6 |
| 6,316,267 B1 | 11/2001 | Bhalgat et al. | 436/86 |
| 6,322,683 B1 * | 11/2001 | Wolk et al. | 204/600 |
| 6,475,441 B1 * | 11/2002 | Parce et al. | 422/100 |
| 6,596,545 B1 * | 7/2003 | Wagner et al. | 436/518 |
| 6,613,581 B1 * | 9/2003 | Wada et al. | 436/518 |
| 6,649,358 B1 * | 11/2003 | Parce et al. | 435/7.2 |

OTHER PUBLICATIONS

Jeon et al., "Generation of Solution and Surface Gradients Using Microfluidic Systems," *Langmuir* 2000, 16, 8311-8316.

Beebe et al., "Microfluidic tectonics: A comprehensive construction platform for microfluidic systems," *PNAS*, 13488-13493, Dec. 5, 2000, vol. 97, No. 25.

* cited by examiner

METHOD OF PERFORMING GRADIENT-BASED ASSAYS IN A MICROFLUIDIC DEVICE

CROSS-REFERENCE TO RELATED APPLICATIONS

This application claims the benefit of U.S. Provisional Application Ser. No. 60/375,156, filed Apr. 24, 2002.

REFERENCE TO GOVERNMENT GRANT

This invention was made with the United States government support awarded by the following agencies: DOD ARPA F33615-98-1-2853. The United States has certain rights in this invention

FIELD OF THE INVENTION

This invention relates generally to microfluidic devices, and in particular, to a method of performing gradient-based assays in a microfluidic device.

BACKGROUND AND SUMMARY OF THE INVENTION

As is known, chemical and biological assays are typically performed in a plurality of multi-well plates. These multi-well plates include a large number of wells that are filled with user desired reagents. The current industry standard requires each multi-well plate to have 96 or 384 wells therein. While each of the wells of the multi-well plates only holds a few microliters, the cumulative volume of reagents required to fill all of the wells can be significant. Since the production of sufficient volumes of the reagents is often time consuming, as well as, expensive, it is highly desirable to provide a method of performing chemical and biological assays utilizing smaller volumes of reagents than prior methods.

Given the large number of wells in the multi-well plates, specialized equipment has been developed in order to quickly and efficiently conduct the chemical and biological assays. For example, specialized equipment is needed to generate the various concentrations of reagents required and to fill each well of the multi-well plate therewith. Further, additional equipment is often necessary to transport the multi-well plates to a user desired location for observation. As such, it is highly desirable to provide a method of performing chemical and biological assays which may be performed more quickly and more simply than prior methods.

Therefore, it is a primary object and feature of the present invention to provide a method of performing chemical and biological assays using smaller volumes of reagent than prior methods.

It is a further object and feature of the present invention to provide a method of performing chemical and biological assays that requires the use of less specialized equipment than prior methods.

It is a still further object and feature of the present invention to provide a method of performing chemical and biological assays that is simpler and less expensive than prior methods.

It is a still further object and feature of the present invention to provide a method of performing chemical and biological assays that is more efficient than prior methods.

In accordance with the present invention, a method of performing a gradient-based assay in a microfluidic device is provided. The method includes the step of providing a microfluidic device having a channel therethrough. The channel is partially defined by a channel while extending along an axis. A plurality of targets are axially spaced along the channel wall. A stream of first fluid is introduced into the channel so as to flow therethrough. The first fluid stream has a predetermined concentration of particles therein. A stream of second fluid is introduced into the channel so as to flow therethrough. The particles in the first fluid stream diffuse into the second fluid stream so as to cause a gradient of concentration of particles in the second fluid stream. The predetermined concentration of particles in the second fluid stream intersect corresponding targets as a second fluid stream flows therepast.

The channel has first and second sides and first and second ends. The channel wall extends along the second side of the channel. The first fluid stream is introduced in the first side of the channel adjacent the first end thereof and the second fluid stream is introduced in the second side of the channel adjacent the first end thereof. The targets are bound to the channel wall or may include a plurality of wells spaced along the channel wall. Further, the targets may include a plurality of sample channels extending from the channel. As such, it is anticipated that portions of the second fluid stream flow into corresponding sample channels. A visual display may be generated in response to the intersection of the second fluid stream and the targets.

In accordance with a further aspect of the present invention, a method of performing a gradient-based assay in a microfluidic device is provided. The microfluidic device has a channel therethrough. The channel is partially defined by a channel wall extending along an axis. The method includes the steps of providing a plurality of targets axially spaced along the channel wall and providing first and second fluids. The first fluid has a predetermined concentration of particles therein. The first and second fluids are passed through the channel such that the particles in the first fluid diffuse into the second fluid so as to cause a gradient of concentration of particles in the second fluid as the second fluid flows through the channel. The predetermined concentration of particles in the second fluid intersect corresponding targets as the second fluid flows therepast.

The channel has first and second sides and first and second ends. The channel wall extends along the second side of the channel. The first fluid is introduced in the first side of the channel adjacent the first end thereof and the second fluid is introduced in the second side of the channel adjacent the second thereof. The targets may be bound to the channel wall; include a plurality of wells spaced along the channel; or include a plurality of sample channels extending from the channel wall wherein portions of the second fluid flow into corresponding sample channels. A visual display is generated in response to the intersection of the second fluid and the targets.

In accordance with a further aspect of the present invention, a method is provided for performing a gradient-based assay in a microfluidic device having a channel therethrough. The channel is partially defined by a channel wall extending along an axis. The method includes the steps of passing a first fluid through the channel and passing a second fluid through a channel. The first fluid has a predetermined concentration of particles therein such that particles in the first fluid diffuse into the second fluid so as to cause a gradient of particles in the second fluid as the second fluid flows through the channel. The second fluid sequentially intersects a series of targets along the channel wall as the second fluid flows through the channel.

The channel has first and second sides and first and second ends and the channel wall extends along the first side of the channel. The method of the present invention may include the additional steps of introducing the first fluid in the first side of the channel adjacent the first end thereof and introducing the second fluid in the second side of the channel adjacent the first end thereof. The targets may be bound to the channel wall; include a plurality of wells spaced along the channel wall; or include a plurality of sample channels extending from the channel. If the targets include a plurality of sample channels, the method includes the additional step of drawing portions of the second fluid into corresponding sample channels as the second fluid passes therepast. A visual display may be generated in response to the intersection of the second fluid and the targets.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
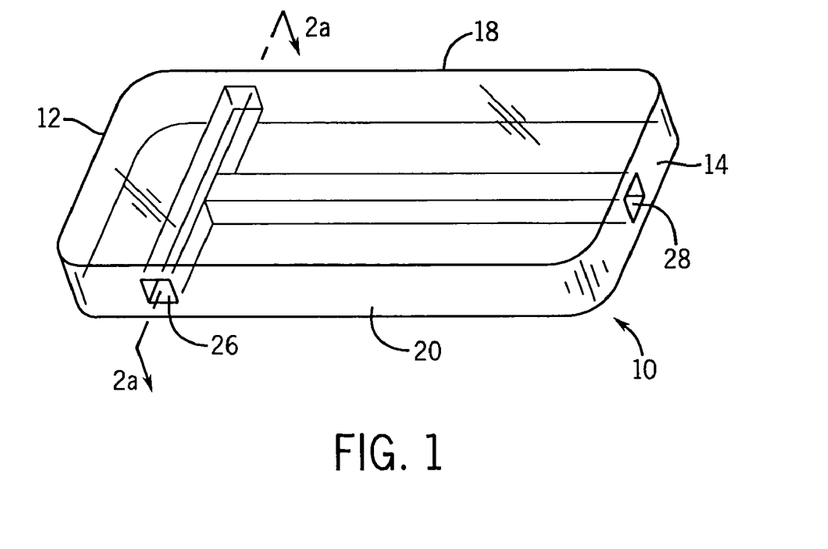
FIG. 1 is an isometric view of a microfluidic device for performing the method of the present invention.

Referring to FIG. 1, a microfluidic device for use in the method of the present invention is generally designated by the reference numeral 10. It is contemplated that microfluidic device 10 be fabricated from polydimethylsiloxane (PDMS). However, microfluidic device 10 may be fabricated from other materials without deviating from the scope of the present invention. Microfluidic device 10 includes first and second ends 12 and 14, respectively, and first and second sides 18 and 20, respectively. It is contemplated to provide one or more channel networks 22a–22c through microfluidic device 10 to effectuate the method of the present invention. The structure of each channel network 22a–22c will be addressed in turn.

Figure 2A:
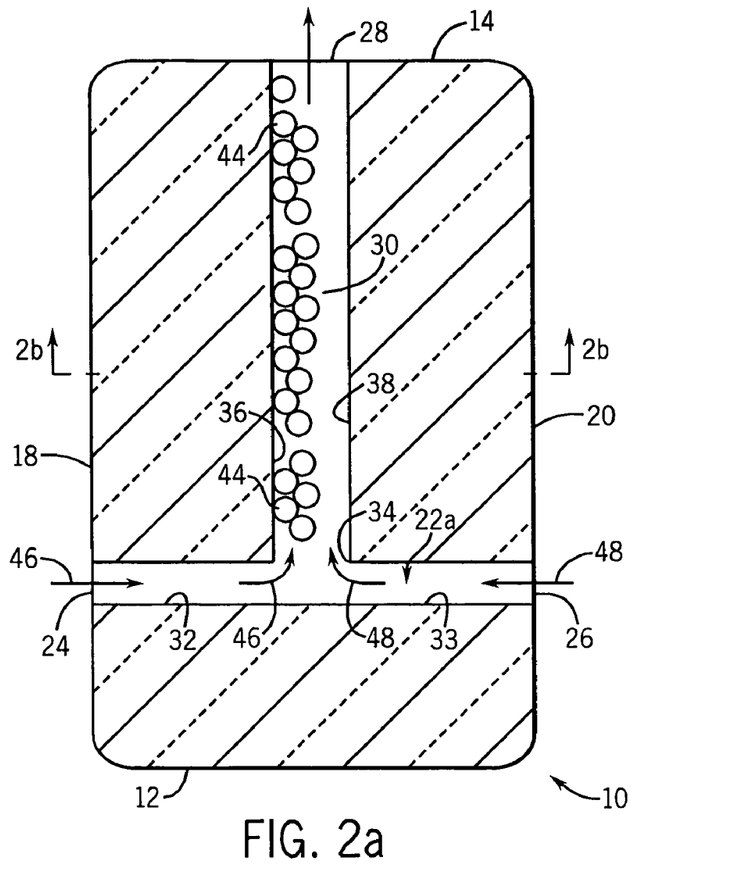
FIGS. 2a and 2b are cross-sectional views of a first embodiment of the microfluidic device of FIG. 1.
Figure 2B:
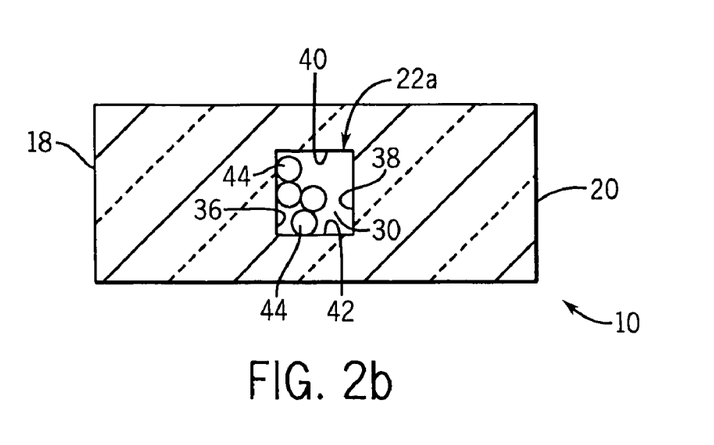

Referring to FIGS. 2a and 2b, a first channel network through microfluidic device 10 is generally designated by the reference numeral 22a. Channel network 22a is generally T-shaped and includes first and second inputs 24 and 26, respectively, and an output 28. In addition, channel network 22a includes central passageway 30, as well as, first and second input passageways 32 and 33, respectively. Central passageway 30 extends along an axis and communicates with output 28. Central passageway 30 is defined by first and second spaced sidewalls 36 and 38, respectively, and upper and lower walls 40 and 42, respectively, such that central passageway has a generally square cross-section.

First input passageway 32 has a first end communicating with first input 24 and a second end communicating with input 34 to central passageway 30. It is intended that first input 24 be connectable to a first fluid source for providing a first inert fluid to channel network 22a. Similarly, second input passageway 33 has a first end communicating with second input 26 and a second end communicating with input 34 to central passageway 30. It is intended that second input 26 be connectable to a second fluid source for providing a second fluid to channel network 22a. The second fluid contains a predetermined concentration of particles of interest (e.g., a virus, a chemical molecule or the like) therein, for reasons hereinafter described.

In order to practice the method of the present invention, a plurality of targets 44 are axially spaced along and affixed to first sidewall 36. By way of example, targets 44 may include molecules, organisms or the like. A stream of first fluid, generally designated by the reference numeral 46, is provided at first input 24. The first stream 46 flows through first input passageway 32 and into central passageway 30 through input 34. A stream of second fluid, generally designated by the reference numeral 48, is provided at second input 26. The second stream 48 flows through second input passageway 33 and into central passageway 30 through input 34. Given the micro-dimensions of central passageway 30, the first and second streams 46 and 48, respectively, flow through central passageway 30 in a laminar flow mode.

As the streams of the first and second fluids 46 and 48, respectively, flow through central passageway 30, the particles in the second fluid diffuse into the first fluid so as to cause a gradient of concentrations to exist in first stream 46. As a result, targets 44 axially spaced along first sidewall 36 are exposed to the gradient of concentrations of particles in first stream 46. Since microfluidic device 10 is fabricated from an optically transparent material, optical changes in targets 44 may be used to determine the effects of various concentrations of particles on targets 44. It can be appreciated that any assay (e.g. drug screening, optimization of chemical reactions, polymer synthesis, etc.) that tests the effects of varying some quantity (e.g. the amount of glucose in cell media, the concentration of some drug, etc) on a specimen (e.g. cells, bacteria, drug target, etc) can be implemented using the method of the present invention.

Figure 3A:
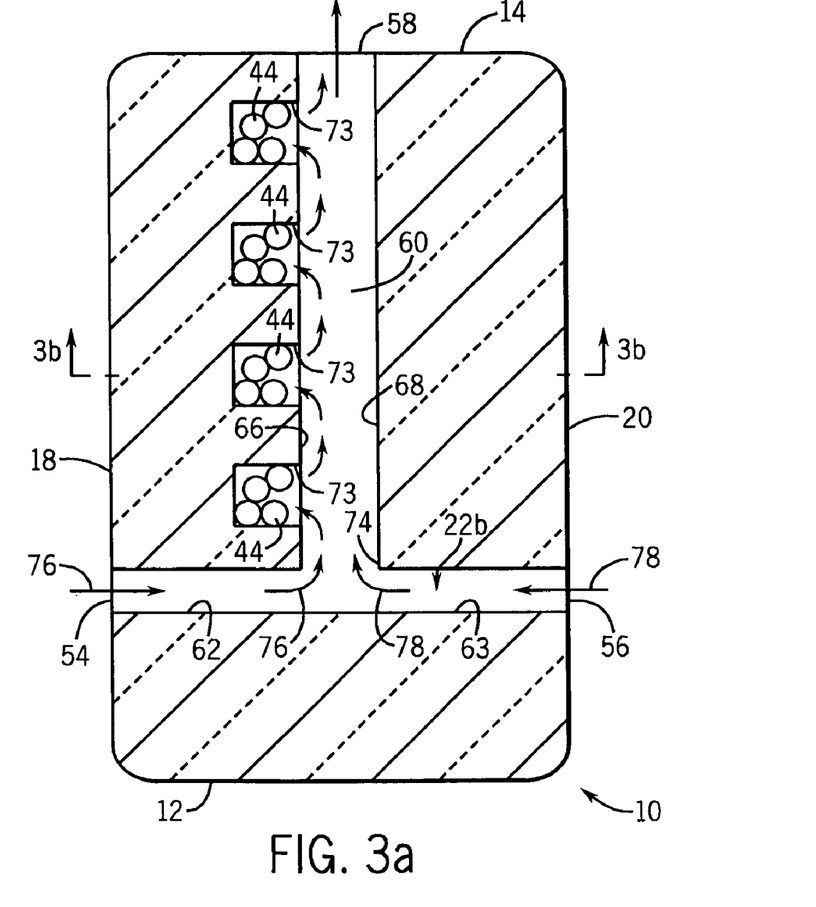
FIGS. 3a and 3b are cross-sectional views of a second embodiment of the microfluidic device of FIG. 1.
Figure 3B:
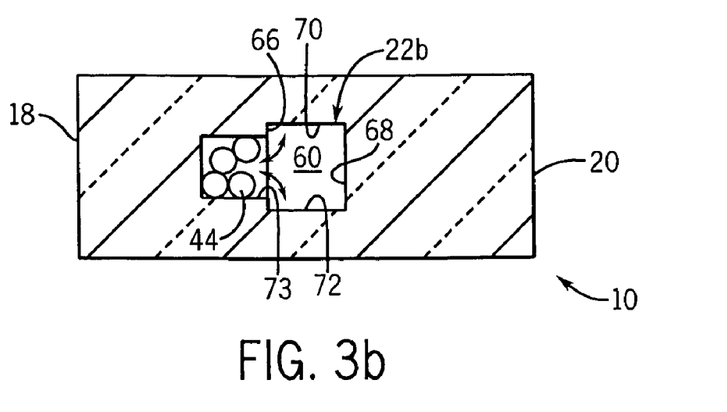

Referring to FIGS. 3a and 3b, an alternate channel network through microfluidic device 10 is generally designated by the reference numeral 22b. Channel network 22b is generally T-shaped and includes first and second inputs 54 and 56, respectively, and an output 58. In addition, channel network 22b includes central passageway 60, as well as, first and second input passageways 62 and 63, respectively. Central passageway 60 extends along an axis and communicates with output 58. Central passageway 60 is defined by first and second spaced sidewalls 66 and 68, respectively, and tipper and lower walls 70 and 72, respectively, such that central passageway has a generally square cross-section. A plurality of depressions or wells 73 are axially spaced and provided in first sidewall 66 for receiving corresponding targets 44 therein, for reasons hereinafter described.

First input passageway 62 has a first end communicating with first input 54 and a second end communicating with input 74 to central passageway 60. It is intended that first input 54 be connectable to a first fluid source for providing a first inert fluid to channel network 22b. Similarly, second input passageway 63 has a first end communicating with second input 56 and a second end communicating with input 74 to central passageway 60. It is intended that second input 56 be connectable to a second fluid source for providing a second fluid to channel network 22b. As heretofore described, the second fluid contains a predetermined concentration of particles of interest (e.g., a virus, a chemical molecule or the like) therein.

In order to practice the method of the present invention, a plurality of targets 44 are provided in each of the wells 73 in first sidewall 66. A stream of first fluid, generally designated by the reference numeral 76, is provided at first input 54. The first stream 76 flows through first input passageway 62 and into central passageway 60 through input 74.

A stream of second fluid, generally designated by the reference numeral 78, is provided at second input 56. The second stream 78 flows through second input passageway 63 and into central passageway 60 through input 74. As heretofore described, given the micro-dimensions of central passageway 60, the first and second streams 76 and 78, respectively, flow through central passageway 60 in a laminar flow mode.

As the streams of the first and second fluids 76 and 78, respectively, flow through central passageway 60, the particles in the second fluid diffuse into the first fluid so as to cause a gradient of concentrations of particles to exist in first stream 76. As a result, targets 44 in wells 73 in first sidewall 66 are exposed to the gradient of concentrations in first stream 76. Since microfluidic device 10 is fabricated from an optically transparent material, optical changes in targets 44 may be used to determine the effects of various concentrations of particles on targets 44.

Figure 4A:
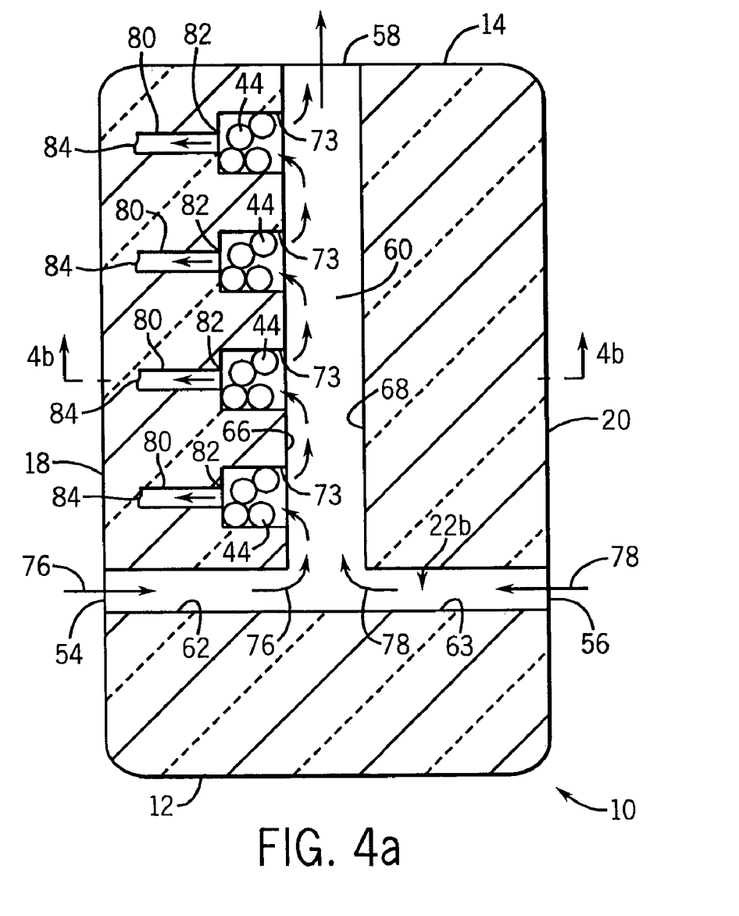
FIGS. 4a and 4b are cross-sectional views of an alternate configuration of the microfluidic device of FIGS. 3a and 3b.
Figure 4B:
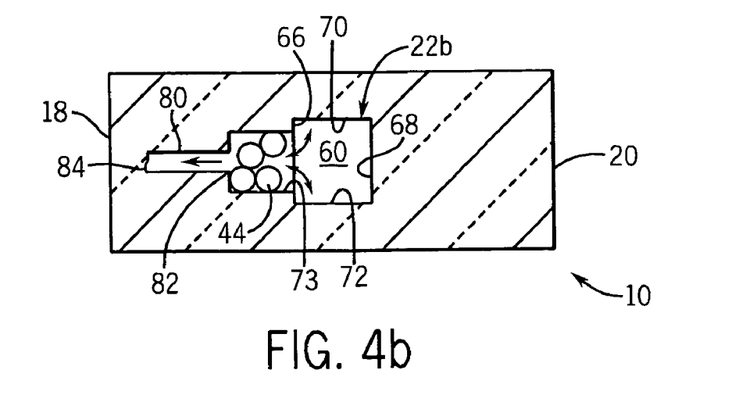

Referring to FIGS. 4a and 4b, it is contemplated to provide a plurality of sample channels 80 within microfluidic device 10. Each sample channel 80 has an input 82 in communication with a corresponding well 73 in first sidewall 66 and an output 84. Sample channels 80 in microfluidic device 10 allow the fluid flowing past targets 44 in wells 73 to be sampled. Outputs 84 of sample channels 80 may be operatively connected to a remote portion of microfluidic device 10 or to an alternate device to allow for further analysis to be conducted on the sampled fluid.

Figure 5A:
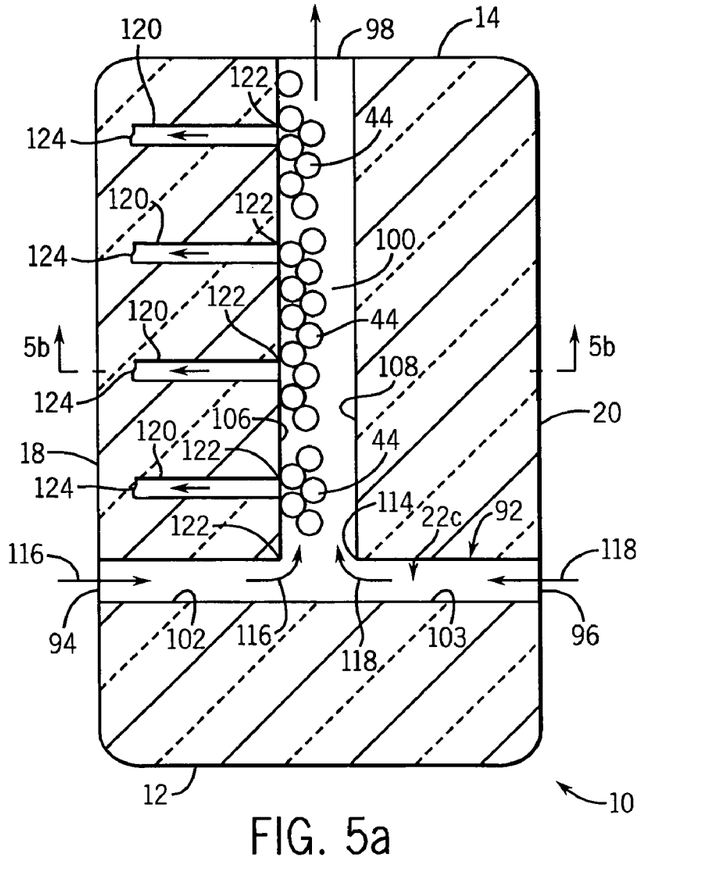
FIGS. 5a and 5b are cross-sectional views of a third embodiment of the microfluidic device of FIG. 1.
Figure 5B:
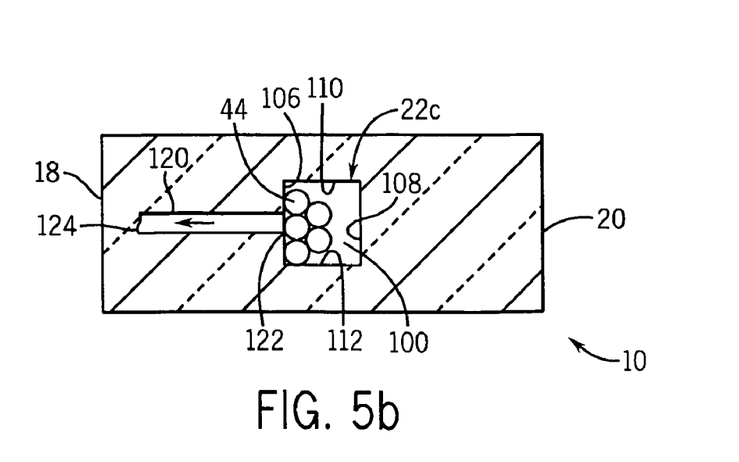

Referring to FIGS. 5a and 5b, a further alternate channel network for microfluidic device 10 is generally designated by the reference numeral 22c. Channel network 22c includes a generally T-shaped portion 92 having first and second inputs 94 and 96, respectively, and an output 98. In addition, portion 92 of channel network 22c includes central passageway 100, as well as, first and second input passageways 102 and 103, respectively. Central passageway 100 extends along an axis and communicates with output 98. Central passageway 100 is defined by first and second spaced sidewalls 106 and 108, respectively, and upper and lower walls 110 and 112, respectively, such that central passageway 100 has a generally square cross-section.

First input passageway 102 has a first end communicating with first input 94 and a second end communicating with input 114 to central passageway 100. It is intended that first input 94 be connectable to a first fluid source for providing a first inert fluid to channel network 22c. Similarly, second input passageway 103 has a first end communicating with second input 96 and a second end communicating with input 114 to central passageway 100. It is intended that second input 96 be connectable to a second fluid source for providing a second fluid to channel network 22c. The second fluid contains a predetermined concentration of particles of interest (e.g., a virus, a chemical molecule or the like) therein, for reasons hereinafter described.

Channel network 22c of microfluidic device 10 further includes a plurality of sample channels 120. Sample channels 120 are generally parallel to each other and perpendicular to central passageway 100. Inputs 122 to sample channels 120 are axially spaced along sidewall 106 and are in communication with central passageway 100. Outputs 124 of sample channels 120 may be operatively connected to a remote portion of microfluidic device 10 or to an alternate device, for reasons hereinafter described.

In order to practice the method of the present invention, a plurality of targets 44 are axially spaced along and affixed to first sidewall 106. A stream of first fluid, generally designated by the reference numeral 116, provided at first input 94, flows through first input passageway 102 and into central passageway 100 through input 114. A stream of second fluid, generally designated by the reference numeral 118, is provided at second input 96. The second stream 118 flows through second input passageway 103 and into central passageway 100 through input 114. As heretofore described, given the micro-dimensions of central passageway 100, the first and second streams 116 and 118, respectively, flow through central passageway 100 in a laminar flow mode.

As the streams of the first and second fluids 116 and 1118, respectively, flow through central passageway 100, the particles in the second fluid diffuse into the first fluid so as to cause a gradient of concentration of particles to exist in first stream 116. As a result, targets 44 affixed to first sidewall 106 are exposed to the gradient of concentrations in first stream 116 Since microfluidic device 10 is fabricated from an optically transparent material, optical changes in targets 44 may be used to determine the effects of various concentrations of particles on targets 44. Sample channels 120 in microfluidic device 10 allow the fluid flowing past targets 44 bound to first sidewall 106 to be sampled for further analysis.

Various modes of carrying out the invention are contemplated as being within the scope of the following claims particularly pointing out and distinctly claiming the subject matter, which is regarded as the invention.

We claim:

1. A method of performing a gradient-based assay in a microfluidic assay, comprising the steps of:
   providing a microfluidic device having a channel therethrough, the channel being partially defined by a channel wall extending along an axis;
   providing a plurality of biological targets axially spaced along the channel wall;
   introducing a stream of first fluid into the channel so as to flow therethrough, the first fluid stream having a predetermined concentration of particles therein;
   introducing a stream of second fluid into the channel so as to flow therethrough in laminar flow with the first fluid stream, the particles in the first fluid stream diffusing into the second fluid stream so as to cause a gradient of concentrations of particles in the second fluid stream such that predetermined concentrations of particles in the second stream intersect corresponding biological targets as the second fluid stream flows therepast;
   monitoring the plurality of biological targets for optical changes, the optical change of each biological target corresponding to the predetermined concentration of particles in the second fluid stream acting thereon;
   selecting one of the predetermined concentrations in response to the optical change of a user-selected biological target; and
   providing a plurality of wells spaced along the channel wall, wherein the plurality of biological targets are located within the wells.

2. The method of claim 1 wherein the channel has first and second fluid sides and first and second ends and wherein the channel wall extends along the second side of the channel.

3. The method of claim 2 wherein the first fluid stream is introduced in the first side of the channel adjacent the first end thereof and wherein the second fluid stream is introduced in the second side of the channel adjacent the first end thereof.

4. The method of claim 1 further comprising the step of generating a visual display in response to the second fluid stream flowing past the biological targets.

5. A method of performing a gradient-based assay in a microfluidic assay, comprising the steps of:
   providing a microfluidic device having a channel therethrough, the channel being partially defined by a channel wall extending along an axis;
   providing a plurality of biological targets axially spaced along the channel wall;
   introducing a stream of first fluid into the channel so as to flow therethrough, the first fluid stream having a predetermined concentration of particles therein;
   introducing a stream of second fluid into the channel so as to flow therethrough in laminar flow with the first fluid stream, the particles in the first fluid stream diffusing into the second fluid stream so as to cause a gradient of concentrations of particles in the second fluid stream such that predetermined concentrations of particles in the second stream intersect corresponding biological targets as the second fluid stream flows therepast;
   monitoring the plurality of biological targets for optical changes, the optical change of each biological target corresponding to the predetermined concentration of particles in the second fluid stream acting thereon;
   selecting one of the predetermined concentrations in response to the optical change of a user-selected biological target; and
   providing a plurality of sample channels extending from the channel, wherein portions of only the second fluid stream flow into corresponding sample channels,
   wherein the biological targets are stationary with respect to the first and second fluid streams flowing through the channel.

6. The method of claim 5 wherein the channel has first and second fluid sides and first and second ends and wherein the channel wall extends along the second side of the channel.

7. The method of claim 6 wherein the first fluid stream is introduced in the first side of the channel adjacent the first end thereof and wherein the second fluid stream is introduced in the second side of the channel adjacent the first end thereof.

8. The method of claim 5 further comprising the step of generating a visual display in response to the second fluid stream flowing past the biological targets.

* * * * *